United States Patent [19]

Scholz et al.

[11] Patent Number: 5,210,075
[45] Date of Patent: May 11, 1993

[54] INTERLEUKIN 6 ANTAGONIST PEPTIDES

[75] Inventors: Wolfgang Scholz; Shiu-Lang Chiang; Gobi Nagarajan, all of San Diego; Thomas J. Lobl, Encinitas, all of Calif.

[73] Assignee: Tanabe Seiyaku Co., Ltd., Osaka, Japan

[21] Appl. No.: 480,868

[22] Filed: Feb. 16, 1990

[51] Int. Cl.$^5$ .................. A61K 37/02; C07K 1/06; C07K 1/08

[52] U.S. Cl. ........................ 514/14; 514/13; 514/15; 530/326; 530/327; 530/328

[58] Field of Search ............. 514/14, 13, 15; 530/326, 327, 328

[56] References Cited

FOREIGN PATENT DOCUMENTS 9006370 6/1990 World Int. Prop. O. .

OTHER PUBLICATIONS

Hirano, et al, *Nature,* vol. 324, pp. 73-76, 1986.
Palaszynski, "Synthetic C Terminal Peptide of IL-1 Functions as a Binding Domain As Well As An Antago Hist For The IL-1 Receptor", Biochemical and Biophysical Research Communication, vol. 147, No. 1, pp. 204-211, 1987.
Auron, et al, "Nucleotide Sequence of Human Monocyte Interleukin 1 Precursor cDNA", Proc. Natl. Acad. Sci. USA, vol. 81 pp. 7907-7911, 1984.

*Primary Examiner*—Merrell C. Cashion, Jr.
*Assistant Examiner*—S. G. Marshall
*Attorney, Agent, or Firm*—Spensley Horn Jubas & Lubitz

[57] ABSTRACT

Peptides and derivatives useful as antagonists to interleukin 6, and uses for the same, are disclosed.

15 Claims, 2 Drawing Sheets

INTERLEUKIN 6 ANTAGONIST PEPTIDES

FIELD OF THE INVENTION

The present invention is related generally to the design and use of peptides as cytokine antagonists and immunomodulators. Short synthetic peptides related to interleukin 6 or to its receptor are identified and shown to be useful as antagonists of interleukin 6. The compounds have application as in vivo or in vitro modulators of immune system responses, and as pharmaceutical agents.

BACKGROUND OF THE INVENTION

The cytokines include a large number of mammalian immunoregulatory hormones that are secreted by cells of the immune system. They exert their biological effects through interaction with specific receptors on cell surfaces. Therefore, the biological response to a cytokine is regulated both by the presence of the cytokine and by the expression of its receptor molecule. Many mammalian diseases, including autoimmune, inflammatory and cancer diseases, are correlated with increased or otherwise altered levels of cytokines or cytokine receptors which may contribute to the misregulation of the immune system and to disease progression. Compounds which are capable of blocking the immunoregulatory or inflammatory effects of cytokines should therefore have significant therapeutic activity with respect to such disease states.

Interleukin 6 (IL-6) is a cytokine with pleiotropic biological activities. IL-6 is produced in response to various stimulators in vitro and in vivo and is detectable in serum during acute bacterial infection and inflammatory responses. Among its many different biological effects, IL-6 is required for the terminal differentiation of B cells to immunoglobulin (Ig) secreting cells (Muraguchi, et al., J. Exp. Med. 167:332, 1988) and for the production of acute phase proteins in vitro (Gauldie, et al., Proc. Natl. Acad. Sci. USA 84:7251, 1987) and in vivo (Geiger, et al., Eur. J. Immunol. 18:717, 1988), the latter being characteristic of a systemic reaction to inflammation or tissue injury. IL-6 is also a potent growth factor for myeloma/plasmacytoma cells; it has been shown to induce differentiation of murine myeloid leukemic M1 cells and neoplastic PC12 neural cells, as well as proliferation and differentiation of certain T-cell subsets; and it has been suggested as being a possible mediator of the pathogenesis of Castleman's disease (a syndrome associated with a benign hyperplasia of the lymph nodes) and Lennert's T-cell lymphoma (Kishimoto, Blood 74:1, 1989). IL-6 is detectable in high amounts in synovial fluids of patients with rheumatoid arthritis (Hirano, et al., Eur. J. Immunol. 18:1797, 1988), an inflammatory disease characterized by high levels of Ig secretion and immune complexes. Immune complex-mediated inflammation is also a hallmark of systemic lupus erythematosus in which kidney failure due to immune complex is a leading cause of death. Several tumor cells such as cardiac myxoma and cervical cancer cells (Kishimoto, et al., Ann. Rev. Immunol. 6:485, 1988) have been shown to produce IL-6. Despite considerable sequence differences between mouse and human IL-6, there seems to be no species restriction.

The human IL-6 receptor (IL-6R) has been cloned from the natural killer-like cell line YT (Yamasaki, et al., Science 241:825, 1988). IL-6 receptors are expressed in high numbers on certain tumor cell lines such as human myelomas, histiocytomas and promyelocytic leukemia cells (Taga, et al., J. Exp. Med. 166:967, 1987).

All publications, patents and other reference materials referred to in the present specification are incorporated herein by reference.

SUMMARY OF THE INVENTION

The present invention relates to peptides having activity as IL-6 antagonists. One object of the invention is to provide peptides which, due to their relatively small size, may be readily synthesized and used either in vivo or in vitro to inhibit one or more of the pleiotropic biological activities mediated by IL-6.

Another object of the invention is to provide compounds, formulations and methods which may be used in the study, treatment or prevention of diseases and conditions including autoimmune diseases, immunoinflammatory diseases, neoplastic diseases, immune system misregulation conditions, acute phase protein production conditions, infectious diseases, and others.

Another object of the invention is to provide structures for the design and synthesis of peptides, peptide derivatives and peptidomimetic compounds useful as IL-6 antagonists and as therapeutic agents.

Another object of the invention is to provide peptide compounds which may be used in the synthesis of antigens for the generation of antibodies, where the resultant antibodies may be used therapeutically, or in vitro, to block IL-6 activity.

DETAILED DESCRIPTION

The peptides of the present invention are represented herein by amino acid sequence formulas wherein the individual amino acids are represented by their standard one-letter or three-letter abbreviations as follows:

| Amino Acid | Three-letter symbol | One-letter symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |

| Amino Acid | Three-letter symbol | One-letter symbol |
|---|---|---|
| Proline | Pro | P |
| Serine | Ser | S |
| Threonine | Thr | T |
| Tryptophan | Trp | W |
| Tyrosine | Tyr | Y |
| Valine | Val | V |

Additional abbreviations used herein include:

| Norleucine | Nle |
|---|---|
| Sarcosine | Sar |
| β-Alanine (3-aminopropionic acid) | β-Ala |
| α-Aminoisobutryic acid (2-methylalanine) | Aib |
| β-Aspartic acid | β-Asp |
| Gamma-aminopentane-1,5-dioic acid | 3-Glu |
| Homoserine | HomoSer |
| Ornithine | Orn |
| Homoarginine | HomoArg |
| Homoproline | HomoPro |
| 4-hydroxyproline | hydroxy-Pro |
| Pyro-glutamic acid | Pyro-Glu |

The peptides of the invention are modeled after amino acid sequences occurring in the IL-6 molecule or in the IL-6 receptor molecule. Although the inventors do not intend to limit the invention to any particular mechanism of activity, it is presently believed that the peptides described correspond to portions of the IL-6 or its cellular receptor that are involved in vivo in cytokine receptor binding or cytokine-mediated signal transduction. Those antagonist peptides that are modeled after a portion of IL-6 are believed to act as IL-6 antagonists by binding to the IL-6 cytokine-specific receptor and thereby inhibiting the transduction of IL-6 cytokine-specific signals. Conversely, those antagonist peptides that are modeled after portions of the IL-6 receptor act as antagonists by binding either to the cytokine itself or to other protein(s) involved in the cytokine-specific signal transduction pathway.

In addition, derivatives of the present antagonist peptides as described hereinafter are useful in the synthesis of antigens which may in turn be used for the generation of antibodies. Such antibodies will, in some cases, themselves be effective in reducing or blocking the in vitro or in vivo activity of IL-6 and/or its receptor. It is believed that the mechanism underlying this effect involves the immuno-complexation of the antibody with either IL-6 or its receptor protein such that IL-6/IL-6 receptor interactions are reduced or blocked with resultant suppression of cytokine-mediated signal transduction.

The peptides of the invention fall into five general classes. The peptides of the first such class are modeled after a portion of the amino acid sequence of the IL-6 cytokine itself, whereas the peptides of the remaining classes are modeled after different portions of the amino acid sequence of the IL-6 receptor molecule.

The first class of peptides includes peptides derived from the p51-70 portion of IL-6 (see Hirano, et al., Nature 324:73, 1986), which has the amino acid sequence (I)

E S S K E A L A E N N L N L P K M A E K
1 2 3 4 5 6 7 8 9 10 11 12 13 14 15 16 17 18 19 20

Peptides of varying length modeled after different portions of the above IL-6 sequence have been synthesized and shown to have activity in inhibiting the IL-6 mediated proliferation of indicator cells. In particular, peptides modeled after the region of amino acids 5-15 (as numbered above), and particularly fragments thereof containing at least amino acids 7-14, are most preferred. Independently, peptides modeled after the region of amino acids 1-10, and particularly fragments thereof containing at least amino acids 3-7, preferred; also independently, peptides modeled after the region of amino acids 11-20, and particularly fragments thereof containing at least amino acids 11-15, are likewise preferred.

It is normally preferred that the peptides of the invention, including those discussed hereinafter, contain the amino acid residues that appear in the corresponding positions of the parent molecule (i.e., IL-6 or the IL-6 receptor). However, as will be described, substitutions of amino acids in particular positions may be employed to preserve or even increase the IL-6 antagonist activity of the subject peptides. In addition, where the subject peptides are to be coupled with proteins or other molecules (as for example where it is desired to form an antigenic product for use in antibody production), it is desirable to incorporate additional amino acids (such as a terminal cysteine and, optionally, one or more adjacent internal glycine spacer residues) into the peptide in order to facilitate such coupling.

The most highly preferred peptides of the invention modeled after the above receptor-binding portion of IL-6 (structure I) are those having the formula $$X^2-(X^1-)7-8-9-10-11-12-13-14(-Y^{1-})-Y^2 \quad (II)$$

and pharmaceutically acceptable salts thereof, wherein
7 is selected from L; I and A; and V, Nle, Sar, β-Ala and Aib;
8 is selected from A; L and I; and V, Nle, Sar, β-Ala and G;
9 is selected from E; pyro-Glu; and D, S, T, Y, β-Asp and 3-Glu;
10 is selected from N; Q, M, W and F; and Y;
11 is selected from N; Q, M, W and F; and Y;
12 is selected from L; I and A; and V, Nle, Sar, β-Ala and Aib;
13 is selected from N; Q, M, W and F; and Y; and
14 is selected from L; I and A; and V, Nle, Sar, β-Ala and Aib;
$X^1$ is optional and, where present, is selected from 6—
5—6—
4—5—6—
3—4—5—6—
2—3—4—5—6— and
1—2—3—4—5—6— wherein
1 is selected from E: pyro-Glu; and D, S, T, Y, β-Asp and 3-Glu;
2 is selected from S; A and M; and T, HomoSer, and Y;
3 is selected from S; A and M; and T, HomoSer, and Y;

4 is selected from K; and R, Orn, HomoArg and H;
5 is selected from E; G and pyro-Glu; and D, S, T, Y, β-Asp and 3-Glu;
6 is selected from A; L and I; and V, Nle, Sar, β-Ala and G;
wherein one or more D-amino acids may be employed among residues 1 to 6;
$Y^1$ is optional and, where present, is selected from —15
—15—16
—15—16—17
—15—16—17—18
—15—16—17—18—19 and
—15—16—17—18—19—20 wherein
15 is selected from P; L and I; and V, Aib, hydroxy-Pro and HomoPro;
16 is selected from K; and R, Orn, HomoArg and H;
17 is selected from M; W, F and Q; and N, Y, H, α-naphthylalanine and β-naphthylalanine;
18 is selected from A; L and I; and V, Nle, Sar, β-Ala and G;
19 is selected from E; pyro-Glu; and D, S, T, Y, β-Asp and 3-Glu;
20 is selected from K; and R, Orn, HomoArg and H;
wherein one or more D-amino acids may be employed among residues 15 to 20;
$X^2$ is a $N^\alpha$-substituent selected from hydrogen, R'CO— and R'—;
$Y^2$ is a carboxyl-terminal substituent selected from hydroxyl, —NH$_2$, —NHR', —NR'$_2$, —OR' and —NHNH$_2$; and
wherein each R' is individually a pharmaceutically suitable substituent group, preferably one selected from linear and branched, unsubstituted and substituted $C_1$-$C_8$ lower alkyls, $C_2$-$C_8$ alkenyls, $C_2$-$C_8$ alkynyls, $C_6$-$C_{14}$ aryls, $C_7$-$C_{14}$ alkaryls, $C_7$-$C_{14}$ aralkyls and $C_3$-$C_{14}$ cycloalkyls, and in the case of —NR'$_2$, from cyclized groups forming (in attachment with the nitrogen atom) a 5-8 membered saturated heterocyclic ring optionally containing an oxygen or nitrogen as a further ring heteroatom.

With respect to the optional $X^1$ and $Y^1$ groups, the group "5-6—" (as defined above) is a preferred $X^1$ group, especially where glycine (G) is chosen for amino acid number 5, and the group "—15" is a preferred $Y^1$ group. As stated above, one or more of the amino acids occurring in the $X^1$ and $Y^1$ portions of the subject peptides may be selected from D-amino acid forms of the listed residues. The use of a D-amino acid would tend to protect the peptide from metabolism in the in vivo environment and thereby increase the effective half-life of the compound in the body. Such a substitution is preferably employed at one or more terminus of the peptide, i.e., in the amino-terminal and/or the carboxyl-terminal residue. Such considerations apply also to the peptides of the invention described hereinafter.

With respect to the amino-terminal substituent $X^2$, hydrogen, lower alkoyl (i.e., $C_1$-$C_8$) and single-ring aroyl substituents are preferred. In this regard, acetyl, propionyl and substituted or unsubstituted benzoyl groups (i.e., R'CO— is CH$_3$CO—, CH$_3$CH$_2$CO— or substituted or unsubstituted (C$_6$H$_5$)CO—) are especially preferred acyl substituents, and will tend to protect the peptide from metabolism in, for example, the in vivo environment and thereby enhance the activity of the compound. Adamantyl—CH$_2$CO— is a preferred bridged cycloalkoyl substituent. These preferred $X^2$ substituents are also preferred for peptides of the invention described hereinafter.

With respect to the carboxyl-terminal substituent $Y^2$, hydroxyl, unsubstituted or lower alkyl-substituted amino, and lower alkoxy or single-ring aryloxy substituents are preferred. Amidating or esterifying substituents of the form —NH$_2$, —NHCH$_3$, —NHCH$_2$CH$_3$, —OCH$_3$ and —O(C$_6$H$_5$) (i.e., —R' is —CH$_3$, —CH$_2$CH$_3$ or —(C$_6$H$_5$)) are especially preferred and will likewise tend to preserve the subject peptides against metabolism. Amidating groups are particularly preferred in this regard. Where an amidating group of the structure —NR'$_2$ is to be cyclic in form, the N-morpholino heterocyclic structure is preferred. These preferred $Y^2$ substituents are also preferred for peptides of the invention described hereinafter.

Where one or more R' groups is itself additionally substituted, preferred substituents include hydroxyl, amino, lower ($C_1$-$C_8$) alkoxyl, and, in the case of aromatic R' groups, the foregoing substituents as well as nitro, chloro and bromo moieties. Such substituents may be used, for example, to alter bioactivity, solubility and/or biodistribution characteristics of the subject peptides. Where R' includes an aryl group, substituents occurring on the meta and/or para positions (i.e., 3'- and/or 4'-positions) are most preferred. Preferred alkaryl forms of R' include (3'-methyl)phenyl and (4'-methyl)phenyl groups. These preferred substituents to R' are also preferred for peptides of the invention described hereinafter.

In cases where the amino-terminal amino acid in the antagonist compound is chosen to be glutamic acid (E), this residue may be substituted with pyro-glutamic acid (a derivative of glutamic acid wherein the carboxyl group on the side chain of the residue is cyclized with the α-amino group of the residue to form a lactam structure). In such instances, no free α-amino group will be present for substitution with an $X^2$ group, and accordingly $X^2$ is not present in the compound and pyro-Glu will be the amino-terminal residue. With respect to compounds of structure II, examples of this optional use of pyro-Glu include instances wherein $X^1$ is chosen to be 1-2-3-4-5-6- and the amino acid in position 1 is pyro-Glu. The substitutability of pyro-Glu for an N-terminal glutamic acid residue is a consideration that applies equally to the peptides discussed hereinafter.

A preferred peptide within the scope of structure II is that having the sequence of structure I. A highly preferred peptide sequence within the scope of structure II is

```
G A L A E N N L N L P
5 6 7 8 9 10 11 12 13 14 15
``` where, in amino acid position 5, glycine (G) has been substituted for the glutamic acid (E) residue occurring in the natural sequence of IL-6 (see structure I).

In the above structure II and in other such peptide structures given hereinafter, for each of the amino acid residue positions designated with a numeral it is particularly preferred that the first-listed amino acid be utilized for that numbered residue. The amino acids listed after this first-listed amino acid are secondarily preferred and, where such secondarily-preferred amino acids are listed in two sets separated by a semicolon, the amino acid(s) of the first-listed set are preferred over those of the second-listed set. Thus, for the amino acid numbered 7 in the above formula, leucine (L) is the most highly preferred residue, while isoleucine (I) and alanine (A) are secondarily preferred, and valine (V), norleucine (Nle), sarcosine (Sar), β-alanine (β-Ala) and α-aminoisobutyric acid (Aib) are also useful but less highly preferred.

In this regard, selections in one or more numbered amino acid positions of amino acid residues other than those that are first-listed in structure II can be expected to yield active peptides in view of the fact that these alternate amino acids have structures that tend to conserve functionally the chemical characteristics of the first-listed residues. Such characteristics include hydrophilicity or hydrophobicity, charge, steric properties, conformational properties and the like. In particular, it is believed that the IL-6 antagonist properties of the peptides of structure II may be due in part to their ability to achieve a generally α-helical conformation under proper solvation conditions, and those skilled in the art will recognize amino acid substitutions that will preserve or enhance such a conformation. It will likewise be understood that amino acid selections that vary from the native sequence occurring in IL-6 (see structure I) may beneficially increase the IL-6 antagonistic activity of the subject peptides, as seen for example in the case of amino acid number 5 of structure II, wherein glycine (G) is in some cases preferably substituted for the native residue, glutamic acid (E). Those practicing the present invention will similarly be able to evaluate substitution choices as described herein by applying the principles of functional group conservation, as recognized in the art, and by employing the assay techniques provided herein.

Where secondarily-preferred residues are employed in the practice of the invention, it is preferred that these be kept to a relative minimum. Thus, it is most preferred in such a case that only one amino acid in the peptide be selected from among the secondarily-preferred residues, with the remaining residues being those described herein as most highly preferred. Somewhat less preferred peptides may be chosen wherein two amino acids are selected from among the secondarily-preferred residues. Where two sets of secondarily-preferred residues are described for a given amino acid position, it is preferable to employ an amino acid from among the more highly preferred (i.e., the first-listed) set, especially where one or more additional substitutions of secondarily-preferred residues are also being employed in the peptide. However, substitutions occurring within the optional $X^1$ and $Y^1$ portions of the peptides are generally contemplated to have less effect on the antagonist activity of the subject peptides than substitutions occurring within the "core" region of the peptides (e.g., "core" amino acids 7-14 in structure II), and therefore greater latitude for substitution may be employed in such $X^1$ and $Y^1$ portions if desired. Such considerations apply also to the peptides of the invention described hereinafter.

In another aspect of the present invention, the peptides described herein may usefully be modified so as to be coupled with other carrier molecules, particularly biomolecules such as polypeptides and proteins, including antigens, antibodies, cell adhesion molecules, etc. Such coupled molecules may be used, for example, as antigens for the generation of antibodies which may be useful in blocking IL-6 activity. In addition, coupling of the present peptides with proteins, such as plasma proteins or antibodies, or with other molecules will alter the biodistribution of characteristics of the peptides and may be utilized to achieve selective delivery to desired locations in the body, altered residence time, and the like.

The peptides of the invention therefore include the IL-6 antagonist compounds as described herein which are additionally modified so as to facilitate coupling to other molecules. In particular, these modified peptides correspond to the structures described herein (e.g., structure II above) with the exception that one of the terminal substituents (i.e., $X^2$ or $Y^2$) is altered to provide a moiety (hereinafter termed $X^c$ or $Y^c$) suitable for coupling. It is preferred that the coupling moiety be chosen so as to afford site-selective coupling with the desired carrier molecule. This may be achieved by selecting a coupling moiety, such as an amino acid residue, which has a reactive group that it suitable for coupling and that does not occur elsewhere in the peptide sequence. Alternatively, if such a reactive group does appear elsewhere in the peptide (particularly in the "core" region, or in the epitope portion of the peptide if antibodies are to be generated thereto), a suitable protective group may be employed to prevent undesirable coupling from occurring at the second reactive group.

A preferred coupling moiety is the amino acid cysteine (C), optionally linked at the amino- or carboxyl-terminus to the remainder of the peptide sequence through one or more adjacent "spacer" amino acid residues (preferably one or more glycine (G) residues). Thus, preferred modified coupling compounds derived from the peptides of structure II correspond to the peptides of that structure wherein $X^c$ is selected from C—(G—)$_n$ or $Y^c$ is selected from (—G)$_n$—C, and wherein n is an integer of from 0 to 15, preferably 1 to 5. Spacer groups other than glycine may be utilized if desired.

It will be recognized that the use of a terminal cysteine residue in this manner will provide a sulfhydryl group useful for coupling with another molecule, as for example in disulfide coupling with a cysteine residue occurring on a carrier molecule. Alternatively, a heterobifunctional linking agent such as succinimidyl-4-(N-maleimidomethyl)cyclohexane-1-carboxylate, sulfosuccinimidyl-4-(N-maleimidomethyl)cyclohexane-1-carboxylate, m-maleimidobenzoyl-N-hydroxylsulfosuccinimide ester, m-maleimidobenzoyl-N-hydroxysuccinimide ester, succinimidyl-4-(p-maleimidophenyl)butyrate, N-succinimidyl(4-iodoacetyl)aminobenzoate, or others may be used. In such instances, the crosslinking agent may first be covalently bonded to, for example, an amino group on the desired carrier molecule, and a terminal Cys-thiol of the modified peptide may then be coupled to the remaining reactive portion of the heterobifunctional linking agent. Examples of the use of such linking agents are well known in the art, and may be found in, for example, "Pierce 1989 Handbook & General Catalog," pages 364-375 (Pierce Chemical Company).

Other linking moieties, such as amino groups as occurring, for example, on a lysine or ornithine coupling moiety, may also be utilized, particularly where the subject peptide does not contain other unprotected amino groups such that site-specific coupling is possible. In this regard, preferred $X^c$ coupling moieties may be selected from K—(G—)$_n$ and Orn—(G—)$_n$, and preferred $Y^c$ coupling moieties may be selected from (—G)$_n$—K and (—G)$_n$—Orn, wherein n is an integer of from 0 to 15, preferably 1 to 5. Here too, spacer groups other than glycine may be used if desired.

For example, the ε-amino group of such a lysine or ornithine coupling moiety may be linked using a haloacetamide, or using phosgene or thiophosgene, to an amino group (e.g., a lysine amino group) on the carrier molecule to which the peptide is to be coupled. Alternatively, a photoactivatable mixed bifunctional crosslinking agent such as N-hydroxysuccinimidyl-4-azidobenzoate may be covalently bonded to the ε-amino group of the desired lysine or ornithine coupling moiety, followed by photoactivation of the linking agent to afford covalent coupling to an amino, hydroxyl or other reactive group on the desired carrier molecule. Procedures for the use of such crosslinking agents are also well known and may be found in the Pierce Handbook cited above.

The considerations noted here with regard to modified peptides containing coupling moieties are applicable also to the antagonist peptides discussed hereinafter, and such modified peptides are all within the scope of the present invention.

A second preferred group of IL-6 related antagonist peptides related to structure I is that having the formula $$X^2-(X^1-)3-4-5-6-7(-Y^1)-Y^2 \quad (III)$$

and pharmaceutically acceptable salts thereof, wherein 3, 4, 5, 6 and 7 are as defined for structure II;

$X^1$ is optional and, where present, is selected from wherein 1 and 2 are as defined for structure II;
$Y^1$ is optional and, where present, is selected from —8
—8—9  and
—8—9—10 wherein 8, 9 and 10 are as defined for structure II; and wherein $X^2$ and $Y^2$ are as defined for structure II.

As with structure II and other such formulas hereinafter, it is most preferred in structure III that the first-listed amino acid be utilized in each numbered position. It is also, as with structure II, most preferred that the terminal substituents $X^2$ and $Y^2$ be hydrogen and hydroxyl, respectively, or that R' be selected from lower alkyl and single-ring aryl moieties where the peptides are acylated, amidated or esterified.

An especially preferred peptide sequence within the scope of structure III is

E S S K E A L A E N
1 2 3 4 5 6 7 8 9 10

Here, as discussed above and as is applicable below, the N-terminal glutamic acid residue (E, position number 1) may optionally be substituted with pyro-Glu.

A third preferred group of IL-6 related antagonist peptide subclass related to structure I is that having the formula $$X^2-11-12-14-15-16(-Y^1)-Y^2 \quad (IV)$$

and pharmaceutically acceptable salts thereof, wherein 11, 12, 13, 14, 15 and 16 are as defined for structure II;
$Y^1$ is optional and, where present, is selected from —17
—17—18
—17—18—19  and
—17—18—19—20 wherein 17, 18, 19 and 20 are as defined for structure II; and
wherein $X^2$ and $Y^2$ are as defined for structure II.

An especially preferred peptide sequence within the scope of structure IV is

N L N L P K M A E K
11 12 13 14 15 16 17 18 19 20

A second general class of IL-6 antagonist peptides according to the invention are derived from the amino acid sequence of the IL-6 receptor. These peptides are modeled after four different portions of the IL-6 receptor sequence, and as with the peptide classes modeled after the structure I region of the IL-6 cytokine (viz., structures II, III and IV), subportions of each of the four IL-6 receptor portions described hereinafter are also independently active as IL-6 antagonists.

One such group of IL-6 antagonist peptides includes compounds modeled after portions of the p268-289 region of the amino acid sequence of the IL-6 receptor (see Yamasaki, et al., Science 241:825, 1988). That region is as follows:

R H V V Q L R A Q E E F G Q G E W S E W S  (V)
1 2 3 4 5 6 7 8 9 10 11 12 13 14 15 16 17 18 19 20 21

Peptides of varying length modeled after different portions of the above IL-6 receptor sequence have been synthesized and shown to have activity in inhibiting the IL-6 mediated proliferation of indicator cells. In particular, peptides modeled after the region of amino acids 4–16 (as numbered above), and particularly fragments thereof containing at least amino acids 6–8, are most preferred. Independently, peptides modeled after the region of amino acids 11–21, and fragments thereof containing at least amino acids 13–16, are also preferred.

The first class of peptides of the invention modeled after the above IL-6 receptor sequence (structure V) has the formula:

$$X^2-(X^1-)4-5-6-7-8-9(-Y^1)-Y^2 \quad (VI)$$

and pharmaceutically acceptable salts thereof, wherein
4 is selected from V; L, I, A and G; and Nle, Sar, β-Ala and Aib;
5 is selected from Q; M, W, F and E; and N and Y;
6 is selected from L; I and A; and V, Nle, Sar, β-Ala and Aib;
7 is selected from R; K; and Orn, HomoArg and H;
8 is selected from A; L and I; and V, Nle, Sar, β-Ala and G; and
9 is selected from Q; M, W, F and E; and N and Y;
$X^1$ is optional and, where present, is selected from 3—
2—3—  and
1—2—3— wherein
1 is selected from R; K; Orn, HomoArg and H;
2 is selected from H; K; R, Orn and HomoArg; and
3 is selected from V; L, I and A; and Nle, Sar, β-Ala, Aib and G;
wherein one or more D-amino acids may be employed among residues 1 to 3;
$Y^1$ is optional and, where present, is selected from —10
—10—11
—10—11—12
—10—11—12—13
—10—11—12—13—14
—10—11—12—13—14—15
—10—11—12—13—14—15—16—17
—10—11—12—13—14—15—16—17—18
—10—11—12—13—14—15—16—17—18—19
—10—11—12—13—14—15—16—17—18—19—20 and
—10—11—12—13—14—15—16—17—18—19—20—21 wherein
10 is selected from E; pyro-Glu; and D, S, T, Y, β-Asp and 3-Glu;
11 is selected from E; pyro-Glu; and D, S, T, Y, β-Asp and 3-Glu;
12 is selected from F; and Y, cyclohexylalanine, α-naphthylalanine and β-naphthylalanine;
13 is selected from G; A, F, L and I; and Nle, β-Ala, Sar and V;
14 is selected from Q; M, W, F and E; and N and Y;
15 is selected from G; A, F, L and I; and Nle, β-Ala, Sar and V;
16 is selected from E; pyro-Glu; and D, S, T, Y, β-Asp and 3-Glu;
17 is selected from W; F, M, and Q; and Y, N, H, α-naphthylalanine and β-naphthylalanine;
18 is selected from S; A and M; and T, HomoSer and Y;
19 is selected from E; pyro-Glu; and D, S, T, Y, β-Asp and 3-Glu;
20 is selected from W; F, M, and Q; and Y, N, H, α-naphthylalanine and β-naphthylalanine;
21 is selected from S; A and M; and T, HomoSer and Y; and wherein one or more D-amino acids may be employed among residues 10 to 21;
$X^2$ is a $N^\alpha$-substituent selected from hydrogen, R'CO— and R'—;
$Y^2$ is a carboxyl-terminal substituent selected from hydroxyl, —NH$_2$, —NHR', —NR'$_2$, —OR' and —NHNH$_2$; and
wherein each R' is as defined above.

As above, use of the first listed amino acid in the numbered positions of the above peptides is especially preferred. Also as above, use of hydrogen and hydroxyl substituents for $X^2$ and $Y^2$, and use of lower alkyl and single-ring aryl substituents for R', are especially preferred.

A preferred peptide within the scope of structure VI is that having the sequence of structure V. One especially preferred peptide within the scope of structure VI is

R H V V Q L R A Q E E
1 2 3 4 5 6 7 8 9 10 11 i.e., structure VI wherein $X^1$ is 1—2—3—4—, $Y^1$ is —10—11, and each amino acid is selected from those described as most highly preferred.

An especially preferred peptide subclass related to the IL-6 receptor and the peptides of structure VI is that having the formula $$X^2\text{---}(X^1\text{---})6\text{---}7\text{---}8(\text{---}Y^1)\text{---}Y^2 \qquad (VII)$$

and pharmaceutically acceptable salts thereof, wherein 6, 7 and 8 are as defined for structure VI;
$X^1$ is optional and, where present, is selected from 5— and
4—5— wherein
5 is as defined for structure VI, and
4 is a L— or D— amino acid selected from G; F, L and I; and A, V, Sar and β-Ala;
$Y^1$ is optional and, where present, is selected from —9
—9—10
—9—10—11
—9—10—11—12
—9—10—11—12—13
—9—10—11—12—13—14
—9—10—11—12—13—14—15 and
—9—10—11—12—13—14—15—16 wherein 9, 10, 11, 12, 13, 14, 15 and 16 are as defined for structure VI; and
wherein $X^2$ and $Y^2$ are as defined for structure VI.

Especially preferred peptides within the scope of structure VII are

G Q L R A Q E E F G Q G E
4 5 6 7 8 9 10 11 12 13 14 15 16 as well as

G Q L R A Q E E F G
G Q L R A Q E E F
G Q L R A Q E E and
Ac—G Q L R A Q E E F G Q G E—NH$_2$ It will be noted here that the most highly preferred amino acid in position number 4 is glycine (G) rather than valine (V), the latter being the residue present in the natural structure of the IL-6 receptor (see structure V).

Another group of peptide antagonists related to the IL-6 receptor sequence V and to the peptides of structure VI has the formula $$X^2\text{---}(X^1\text{---})13\text{---}14\text{---}15\text{---}16(\text{---}Y^1)\text{---}Y^2 \qquad (VIII)$$

and pharmaceutically acceptable salts thereof, wherein 13, 14, 15 and 16 are as defined for structure VI;
$X^1$ is optional and, where present, is selected from 12— and
11—12— wherein 11 and 12 are as defined for structure VI;
$Y^1$ is optional and, where present, is selected from

—17
—17—18

—17—18—19

—17—18—19—20

—17—18—19—20—21 and

—17—18—19—20—21—22 wherein 17, 18, 19, 20, 21 and 22 are as defined for structure VII; and wherein $X^2$ and $Y^2$ are as defined for structure VI.

An especially preferred peptide within the scope of structure VIII is

```
E   F   G   Q   G   E   W   S   E   W   S
11  12  13  14  15  16  17  18  19  20  21
```

As above, the N-terminal glutammic acid residue (E) may optionally be substituted with pyro-Glu.

A second class of IL-6 antagonist peptides modeled after a portion of the amino acid sequence of the IL-6 receptor includes peptides modeled after the receptor sequence (p48–66)

```
A G S H P S R W A G M  G  R  R  L  L  L  R   (IX)
1 2 3 4 5 6 7 8 9 10 11 12 13 14 15 16 17 18 19
```

Here, too, peptides of varying length modeled after different portions of the above IL-6 receptor sequence have been synthesized and shown to have activity in inhibiting the IL-6 mediated proliferation of indicator cells. In particular, peptides modeled after the region of amino acids 2–14 (as numbered above), and fragments thereof containing at least amino acids 4–7, are most preferred. Independently, peptides modeled after the region of amino acids 10–19, and fragments thereof containing at least amino acids 12–17, are likewise preferred.

A first group of peptide antagonists modeled after the IL-6 receptor sequence of structure IX has the formula $$X^2—(X^1—)4—5—6—7(—Y^1)—Y^2 \qquad (X)$$

and pharmaceutically acceptable salts thereof, wherein
4 is selected from H; K; and R, Orn and HomoArg;
5 is selected from P; L and I; and V, Aib, hydroxy-Pro and HomoPro;
6 is selected from S; A and M; and T, HomoSer and Y; and
7 is selected from R; K; and Orn, HomoArg and H;
$X^1$ is optional and, where present, is selected from

3—

2—3— and

1—2—3— wherein
1 is selected from A; L and I; and V, Nle, Sar, β-Ala and G;
2 is selected from G; A, F, L and I; and Sar and V;
3 is selected from S; A and M; and T, HomoSer and Y; wherein one or more D-amino acids may be employed among residues 1 to 3;
$Y^1$ is optional and, where present, is selected from

—8

—8—9

—8—9—10

—8—9—10—11

—8—9—10—11—12

—8—9—10—11—12—13

—8—9—10—11—12—13—14

—8—9—10—11—12—13—14—15

—8—9—10—11—12—13—14—15—16

—8—9—10—11—12—13—14—15—16—17

—8—9—10—11—12—13—14—15—16—17—18 and

—8—9—10—11—12—13—14—15—16—17—18—19 wherein
8 is selected from W; F, M and Q; and Y, N, H, α-naphthylalanine and β-naphthylalanine;
9 is selected from A; L and I; and V, Nle, Sar, β-Ala and G;
10 is selected from G; A, F, L and I; and Sar and V;
11 is selected from M; W, F and Q; and Y, N, H, α-naphthylalanine and β-naphthylalanine;
12 is selected from G; A, F, L and I; and Sar, V, Nle and β-Ala;
13 is selected from R; K; and Orn, HomoArg and H;
14 is selected from R; K; and Orn, HomoArg and H;
15 is selected from L; I and A; and V, Nle, Sar, β-Ala and Aib;
16 is selected from L; I and A; and V, Nle, Sar, β-Ala and Aib;
17 is selected from L; I and A; and V, Nle, Sar, β-Ala and Aib;
18 is selected from R; K; and Orn, HomoArg and H;
19 is selected from S; A and M; and T, HomoSer and Y;
wherein one or more D-amino acids may be employed among residues 8 to 19;
$X^2$ is a $N^\alpha$-substituent selected from hydrogen, R'CO— and R'—;
$Y^2$ is a carboxyl-terminal substituent selected from hydroxyl, —NH$_2$, —NHR', —NR'$_2$, OR— and —NHNH$_2$; and
wherein each R' is as defined above.

As above, use of the first listed amino acid in the numbered positions of the above peptides is especially preferred. Also as above, use of hydrogen and hydroxyl substituents for $X^2$ and $Y^2$, and use of lower alkyl and single-ring aryl substituents for R' are especially preferred.

A preferred peptide within the scope of structure X is the sequence given by structure IX. Other preferred antagonist peptides within the scope of structure X have the sequences

```
H  P  S  R  W  A  G  M  G  R  R
4  5  6  7  8  9  10 11 12 13 14
``` which is especially preferred, and

```
A G S H P S R W A G
1 2 3 4 5 6 7 8 9 10
```

In addition, the modified peptide

```
C G H P S R W A G  M  R  R
2 3 4 5 6 7 8 9 10 11 12 13 14
``` which contains the coupling moiety C—G— at the amino terminus, has been coupled to a carrier molecule as described hereinafter and found to be particularly useful in the subsequent generation of antibodies.

A second group of antagonist peptides related to structure X has the formula $$X^2-(X^1-)12-13-14-15-16-17(-Y^1)-Y^2 \quad (XI)$$

and pharmaceutically acceptable salts thereof, wherein 12, 13, 14, 15, 16 and 17 are as defined for structure X; $X^1$ is optional and, where present, is selected from 11— and

10—11— wherein 10 and 11 are as defined for structure X; $Y^1$ is optional and, where present, is selected from —18 and

—18—19 wherein 18 and 19 are as defined for structure X; and
wherein $X^2$ and $Y^2$ are as defined for structure X.

A particularly preferred peptide within the scope of structure XI has the sequence

```
G  M  G  R  R  L  L  L  R  S
10 11 12 13 14 15 16 17 18 19
```

A third general class of IL-6 antagonist peptides modeled after a portion of the amino acid sequence of the IL-6 receptor includes peptides modeled after the receptor sequence (p250-267):

```
M V K D L Q H H C V  I  H  D  A  W  S  G  (XII)
1 2 3 4 5 6 7 8 9 10 11 12 13 14 15 16 17 18
```

Again, peptides of varying length modeled after different portions of the above IL-6 receptor sequence have been synthesized and shown to have activity in inhibiting the IL-6 mediated proliferation of indicator cells. In particular, peptides modeled after the region of amino acids 1-14 (as numbered above), and fragments thereof containing at least amino acids 3-5, are most preferred. In addition, compounds modeled after the region of amino acids 8-18, and fragments thereof containing at least amino acids 10-13, are also preferred.

A first group of peptides of the invention modeled after the above IL-6 receptor sequence (structure XII) has the formula $$X^2-(X^1-)3-4-5(-Y^1)-Y^2 \quad (XIII)$$

and pharmaceutically acceptable salts thereof, wherein
3 is selected from K; and R, Orn, HomoArg and H;
4 is selected from D; E; and S, T, Y, β-Asp and 3-Glu; and
5 is selected from L; I and A; and V, Nle, Sar, β-Ala and Aib;
$X^1$ is optional and, where present, is selected from 2— and

1—2— wherein
1 is selected from M; W, F and Q; and N, Y, H, α-naphthylalanine and β-naphthylalanine;
2 is selected from V; L, I and A; and Nle, Sar, β-Ala, Aib and G;
wherein one or more D-amino acids may be employed among residues 1 and 2;
$Y^1$ is optional and, where present, is selected from

—6

—6—7

—6—7—8

—6—7—8—9

—6—7—8—9—10

—6—7—8—9—10—11

—6—7—8—9—10—11—12

—6—7—8—9—10—11—12—13

—6—7—8—9—10—11—12—13—14

—6—7—8—9—10—11—12—13—14—15

—6—7—8—9—10—11—12—13—14—15—16

—6—7—8—9—10—11—12—13—14—15—16—17 and

—6—7—8—9—10—11—12—13—14—15—16—17—18 wherein
6 is selected from Q; M, W, F and E; and N and Y;
7 is selected from H; K; and R, Orn and HomoArg;
8 is selected from H; K; and R, Orn and HomoArg;
9 is selected from S; A and M; and T, HomoSer and Y;
10 is selected from V; L, I and A; and Nle, Sar, β-Ala, Aib and G;
11 is selected from I; L and A; and V, Nle, Sar, β-Ala and Aib;
12 is selected from H; K; and R, Orn and HomoArg;
13 is selected from D; E; and S, T, Y, β-Asp and 3-Glu;
14 is selected from A; L and I; and V, Nle, Sar, β-Ala and G;
15 is selected from W; F and M; and Y, H, α-naphthylalanine and β-naphthylalanine;
16 is selected from S; A and M; and T, HomoSer and Y;
17 is selected from G; A, F, L and I; and Sar, V, Nle and β-Ala; and
18 is selected from L; I and A; and V, Nle, Sar, β-Ala and Aib;
wherein one or more D-amino acids may be employed among residues 6 to 18;

$X^2$ is a $N^\alpha$-substituent selected from hydrogen, R'CO— and R'—;

$Y^2$ is a carboxyl-terminal substituent selected from hydroxyl, —$NH_2$, —NHR', —$NR'_2$, —OR' and —$NHNH_2$; and

```
R  L  F  Q  N  S  P  A  G  D  F  Q  E  P  C  Q  Y  S  Q  E  S  Q  L  F     (XV)
1  2  3  4  5  6  7  8  9 10 11 12 13 14 15 16 17 18 19 20 21 22 23 24
``` wherein each R' is as defined above.

As above, use of the first listed amino acid in the numbered positions of the above peptides is especially preferred. Also as above, use of hydrogen and hydroxyl substituents for $X^2$ and $Y^2$, and use of lower alkyl and single-ring aryl substituents for R', are especially preferred.

An especially preferred peptide within the scope of structure XIII is

```
M  V  K  D  L  Q  H  H  S  V  I  H  D  A
1  2  3  4  5  6  7  8  9 10 11 12 13 14
```

It has been discovered in investigations relating to the present invention that the peptide sequence

```
F   T   T   W   M  V  K  D  L  Q  H
-4  -3  -2  -1   1  2  3  4  5  6  7
``` which occurs in the natural structure of the IL-6 receptor is, unlike the antagonist compounds of the present invention, an enhancer of to IL-6 activity.

It will be noted that amino acid number 9 in structure XIII is preferably serine (S), whereas the corresponding residue from the natural sequence of the IL-6 region (structure XII, residue 9), is cysteine (C). The substitution of serine, or its secondarily-preferred residues, for cysteine is believed to enhance the activity of the present compounds by eliminating a reactive sit (for oxidation and/or disulfide formation) of the subject peptides.

A second group of peptides related to the IL-6 receptor and the peptides of structure XIII is that having the formula $$X^2—(X^1—)10—11—12—13(—Y^1)—Y^2 \quad \text{(XIV)}$$

and pharmaceutically acceptable salts thereof, wherein 10, 11, 12 and 13 are as defined for structure XIII; $X^1$ is optional and, where present, is selected from 9— and

8—9— wherein 8 and 9 are as defined for structure XIII, $Y^1$ is optional and, where present, is selected from

—14

—14—15

—14—15—16

—14—15—16—17 and

—14—15—16—17—18 wherein 14, 15, 16, 17 and 18 are as defined for structure XIII; and wherein $X^2$ and $Y^2$ are as defined for structure XIII.

A fourth general class of IL-6 antagonist peptides modeled after a portion of the amino acid sequence of the IL-6 receptor includes peptides modeled after the p132-155 region of the IL-6 receptor sequence, which is as follows:

Peptides of varying length modeled after different portions of the above IL-6 receptor sequence have been synthesized and shown to have activity in inhibiting the IL-6 mediated proliferation of indicator cells. In particular, peptides modeled after the region of amino acids 8-24 (as numbered above), and fragments thereof containing at least amino acids 15-21, are most preferred. Independently, peptides modeled after the region of amino acids 1-20, and fragments thereof containing at least amino acids 8-12, are likewise preferred.

A first class of peptides of the invention modeled after the above IL-6 receptor sequence (structure XV) has the formula $$X^2—(X^1—)15—16—17—18—19—20—21(—Y^{1-})—Y^2 \quad \text{(XVI)}$$

and pharmaceutically acceptable salts thereof, wherein
15 is selected from S; A and M; and T, HomoSer and Y;
16 is selected from Q; M, W, F and E; and N and Y;
17 is selected from Y; F; and cyclohexylalanine, α-naphthylalanine and β-naphthylalanine;
18 is selected from S; A and M; and T, HomoSer and Y;
19 is selected from Q; M, W, F and E; and N and Y;
20 is selected from E; pyro-Glu; and D, S, T, Y, β-Asp and 3-Glu; and
21 is selected from S; A and M; and T, HomoSer and Y;
$X^1$ is optional and, where present, is selected from

14—

13—14—

12—13—14—

11—12—13—14—

10—11—12—13—14—

9—10—11—12—13—14—

8—9—10—11—12—13—14—

7—8—9—10—11—12—13—14—

6—7—8—9—10—11—12—13—14—

5—6—7—8—9—10—11—12—13—14—

4—5—6—7—8—9—10—11—12—13—14—

3—4—5—6—7—8—9—10—11—12—13—14—

2—3—4—5—6—7—8—9—10—11—12—13—14— and

1—2—3—4—5—6—7—8—9—10—11—12—13—14— wherein
1 is selected from R; K; and Orn, HomoArg and H;
2 is selected from L; I and A; and V, Nle, Sar, β-Ala and Aib;

3 is selected from F; and Y, cyclohexylalanine, α-naphthylalanine and β-naphthylalanine;

4 is selected from Q; M, W, F and E; and N and Y;

5 is selected from N; Q, M, W and F; and Y;

6 is selected from S; A and M; and T, HomoSer an Y;

7 is selected from P; L and I; and V, Aib, hydroxy-Pro and HomoPro;

8 is selected from A; L and I; and V, Nle, Sar, β-Ala and G;

9 is selected from G; A, F, L and I; and Sar and V;

10 is selected from D; E; and S, T, Y, β-Asp and 3-Glu;

11 is selected from F; and Y, cyclohexylalanine, α-naphthylalanine and β-naphthylalanine;

12 is selected from Q; M, W, F and E; and N and Y;

13 is selected from E; pyro-Glu; and D, S, T, Y, β-Asp and 3-Glu; and 14 is selected from P; L and I; and V, Aib, hydroxy-Pro and HomoPro;

wherein one or more D-amino acids may be employed among residues 1 to 14;

$Y^1$ is optional and, where present, is selected from

—22

—22—23 and

—22—23—24 wherein 22 is selected from Q; M, W, F and E; and N and Y;

23 is selected from L; I and A; and V, Nle, Sar, β-Ala and Aib; and 24 is selected from F; and Y, cyclohexylalanine, α-naphthylalanine and β-naphthylalanine;

wherein one or more D-amino acids may be employed among residues 22 to 24;

$X^2$ is a $N^\alpha$-substituent selected from hydrogen, R'CO— and R'—;

$Y^2$ is a carboxyl-terminal substituent selected from hydroxyl, —$NH_2$, —NHR', —$NR'_2$, —OR' and —$NHNH_2$; and wherein each R' is as defined above.

As above, use of the first listed amino acid in the numbered positions of the above peptides is especially preferred. Also as above, use of hydrogen and hydroxyl substituents for $X^2$ and $Y^2$, and use of lower alkyl and single-ring aryl substituents for R', are especially preferred.

It will be noted that amino acid number 15 in structure XVI is preferably serine (S), whereas the corresponding residue from the natural sequence of the IL-6 region (structure XV, residue 15), is cysteine (C). The substitution of serine, or its secondarily-preferred residues, for cysteine is believed to enhance the activity of the present compounds by eliminating a reactive site (for oxidation and/or disulfide formation) of the subject peptides.

A preferred peptide within the scope of structure XVI is the sequence of structure XV. An especially preferred peptides within the scope of structure XVI has the sequence

E  P  S  Q  Y  S  Q  E  S  Q  L  F
13 14 15 16 17 18 19 20 21 22 23 24 where pyro-Glu may optionally be substituted for glutamic acid (E) in the N-terminal position.

A second group of peptides related to the IL-6 receptor region of structure XV and to the peptides of structure XVI is that having the formula $$X^2—(X^1—)8—9—10—11—12(—Y^1—)—Y^2 \quad (XVII)$$

and pharmaceutically acceptable salts thereof, wherein 8, 9, 10, 11 and 12 are as defined for structure XVI; $X^1$ is optional and, where present, is selected from

7—

6—7—

5—6—7—

4—5—6—7—

3—4—5—6—7—

2—3—4—5—6—7— and

1—2—3—4—5—6—7— wherein 1, 2, 3, 4, 5, 6 and 7 are as defined for structure XVI;

$Y^1$ is optional and, where present, is selected from

—13

—13—14

—13—14—15—16

—13—14—15—16—17 and

—13—14—15—16—17—18—19—20 wherein 13, 14, 15, 16, 17, 18, 19 and 20 are as defined for structure XVI; and wherein $X^2$ and $Y^2$ are as defined for structure XVI.

Especially preferred peptides within the scope of structure XVII are

A G D F Q E P S Q Y S Q E
8 9 10 11 12 13 14 15 16 17 18 19 20 which is especially preferred, and

R L F Q N S P A G D F Q
1 2 3 4 5 6 7 8 9 10 11 12

Synthesis and Formulation of Peptides

Peptides of this invention may be synthesized by the solid phase peptide synthesis (or Merrifield) method, by solution phase synthesis, or by other techniques known in the art. The Merrifield synthesis established and widely used, and experimental procedures, are described in the following references:

Merrifield, J. Am. Chem. Soc., 85, 2149-2154 (1963)

Meienhofer, in "Hormonal Proteins and Peptides," ed. C. H. Li, Vol. 2 (Academic Press, 1973), p. 48-267

Barany and Merrifield in "The Peptides," eds. E. Gross and J. Meienhofer, Vol. 2 (Academic Press, 1980), p. 3-285

In this preferred method a peptide of any desired length and of any desired sequence is produced through the stepwise addition of amino acids to a growing peptide chain which is bound by a covalent bond to a solid resin particle. Automated synthesis may be employed in this method.

In the preferred application of this method the C-terminal end of the growing peptide chain is covalently bound to a resin particle and amino acids having protected amino groups are added in the stepwise manner indicated above. A preferred amino protecting group is the t-Boc group, which is stable to the condensation conditions and yet is readily removable without destruction of the peptide bonds or racemization of chiral centers in the peptide chain. At the end of the procedure the final peptide is cleaved from the resin, and any remaining protecting groups are removed, by treatment under acidic conditions such as, for example, with a mixture of hydrobromic acid and trifluoroacetic acid, with trifluoromethane sulfonic acid or with liquified hydrofluoric acid.

The cleaved peptides are isolated and purified by means well known in the art such as, for example, lyophilization following, for example, reversed phase (preferably) or normal phase high pressure liquid chromatography (HPLC), or by either size exclusion or partition chromatography on polysaccharide gel media such as Sephadex G-25, or countercurrent distribution. The composition of the final peptide may be confirmed by amino acid analysis after degradation of the peptide by standard means, by amino acid sequencing techniques, or by FAB-MS techniques.

Salts of carboxyl groups of the peptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like. In all such procedures and in other synthetic procedures provided herein, the pH should be kept below approximately 8 in order to avoid complications such as racemization, demamidation, peptide degradation or other undesirable side reactions.

Acid salts of the polypeptides may be prepared by contacting the polypeptide with one or more equivalents of the desired inorganic or organic acid, such as, for example, hydrochloric acid, acetic acid or citric acid.

Esters of carboxyl groups of the polypeptides may be prepared by any of the usual means known in the art for converting a carboxylic acid or precursor to an ester. One preferred method for preparing esters of the present polypeptides, when using the Merrifield synthesis technique described above, is to cleave the completed polypeptide from the resin in the presence of the desired alcohol either under basic or acidic conditions, depending upon the resin. Thus the C-terminal end of the peptide when freed from the resin is directly esterified without isolation of the free acid. Alternatively, especially where the desired peptide contains one or more glutamic acid or aspartic acid residues, C-terminal amino acid esters may be made using solution phase synthesis wherein the a C-terminal residue bearing the desired ester functionality is incorporated.

Amides of the polypeptides of the present invention may also be prepared by techniques well known in the art for converting a carboxylic acid group or precursor to an amide. A preferred method for amide formation at the C-terminal carboxyl group is to synthesize the peptides by solid phase methods on a benzhydrylamine resin, and thereafter to cleave the polypeptide from a solid support with an appropriate acid. If the desired amide is to include a secondary or tertiary amino group, then the amide may be synthesized using solution phase techniques wherein an amidated C-terminal residue bearing the desired amide functionality is incorporated.

N-Acyl derivatives of an amino group of the present polypeptides may be prepared by utilizing an N-acyl protected amino acid for the final condensation, or by acylating a protected or unprotected peptide. Acylation may be carried out using standard acylating reagents such as acyl halides, anhydrides, acyl imidazoles, and the like prior to deprotection of the residue side chains.

The coupling, deprotection/cleavage reactions and preparation of derivatives of the subject polypeptides are suitably carried out at temperatures between about $-10°$ and $+80°$ C., most preferably about 20°-25° C. The exact temperature for any particular reaction will, of course, be dependent upon the substrates, reagents, solvents and so forth, all being well within the skill of the practitioner. Illustrative reaction conditions for these processes may be gleaned from the examples.

The peptides of this invention may also be synthesized using any techniques that are known to those in the peptide art, for example, those described in HoubenWeyl, Methoden Der Organischen Chemie, Vol. 15-II, pg. 1-806 (1974), Georg-Thieme-Verlag, Stuttgart.

Useful pharmaceutical carriers for the preparation of the peptide-containing pharmaceutical compositions hereof can be solids, liquids or gases, thus, the compositions can take the form of tablets, pills, capsules, powders, enterically coated or other protected formulations (such as by binding an ion exchange resins or other carriers, or packaging in lipid protein vesicles or adding additional terminal amino acids or replacing a terminal amino acid in the L-form with one in the D-form), sustained release formulations solutions (e.g., ophthalmic drops), suspensions, elixirs, aerosols, and the like. Water, saline, aqueous dextrose, and glycols are preferred liquid carriers, particularly (when isotonic) for injectable solutions. The carrier can be selected from the various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monosterate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjustic osmotic pressure, buffers, and the like. Suitable pharmaceutical carriers and their formulations are described in "Remington's Pharmaceutical Sciences" by E.W. Martin. Such compositions will, in any event, contain an effective amount of the active compound together with a suitable amount of carrier so as to prepare the proper dosage form for proper administration to the host.

In the practice of the therapeutic methods of the present invention, an effective amount of polypeptide or derivative thereof, or a pharmaceutical composition containing same, as defined above, is administered via any of the usual and acceptable methods known in the art, either singly or in combination with another compound or compounds of the present invention or other pharmaceutical agents such as immunosuppressants, antihistamines, corticosteroids, and the like. These compounds or compositions can thus be administered orally, sublingually, topically (e.g., on the skin or in the eyes), parenterally (e.g., intramuscularly, intravenously, subcutaneously or intradermally), or by inhalation, and in the form of either solid, liquid or gaseous dosage including tablets, suspensions, and aerosols, as is discussed in more detail above. The administration can be conducted in single unit dosage form with continuous therapy or in single dose therapy ad libitum.

In one preferred embodiment, the therapeutic methods of the present invention are practiced when the relief of symptoms is specifically required or perhaps imminent; in another preferred embodiment, the method hereof is effectively practiced as continuous or prophylactic treatment.

In the practice of the therapeutic methods of the invention, the particular dosage of pharmaceutical composition to be administered to the subject will depend on a variety of considerations including the nature of the disease, the severity thereof, the schedule of administration, the age and physical characteristics of the subject, and so forth. Proper dosages may be established using clinical approaches familiar to the medicinal arts. It is presently believed that dosages in the range of 0.1 to 100 mg of peptide per kilogram of subject body weight will be useful, and a range of 1 to 100 mg per kg generally preferred, where administration is by injection or ingestion. Topical dosages may utilize formulations containing generally as low as 0.1 mg of peptide per ml of liquid carrier or excipient, with multiple daily applications being appropriate.

The following examples are given to enable those skilled in the art to more fully understand and practice the present invention. They should not be construed as a limitation upon the scope of the invention, but merely as being illustrative and representative thereof.

EXAMPLES

Representative IL-6 antagonist peptides of the present invention have been prepared and assayed according to techniques known to the art. Unless mentioned otherwise, all chemicals utilized in these procedures were of analytical grade and purchased from standard commercial sources.

Peptides according to the invention were synthesized by the solid phase peptide synthesis method (Merrifield, J. Am. Chem. Soc. 85:2149, 1963). The amino acid numbering of peptides derived from the IL-6 receptor (IL-6R) sequence is based on the published sequence of Yamasaki, et al, (Science 241:825, 1988), and numbering of peptides derived from the IL-6 sequence is based on the sequence of IL-6 as published by Hirano, et al. (Nature 324:73, 1986). The numbering refers to the position of the amino acids in the mature protein after excision of the signal sequence. Activity was established in an IL-6-dependent B9.9 cell proliferation assay as described hereunder.

TABLE I

| Sequences of selected IL-6 or IL-6R Derived Peptides | | | |
|---|---|---|---|
| Peptide Sequence | MW | Active | Location |
| RYRAERSKTFT | 1414.59 | No | IL-6R, p 237-247 |
| GALAENNLNLP | 1125.25 | Yes | IL-6, G+ p 56-65 |
| GQLRAQEEFGQGE | 1448.51 | Yes | IL-6R, G+ p 272-283 |

TABLE I-continued

| Sequences of selected IL-6 or IL-6R Derived Peptides | | | |
|---|---|---|---|
| Peptide Sequence | MW | Active | Location |
| HPSRWAGMGRR | 1310.51 | Yes | IL-6R, p 51-61 |
| MVKDLQHHSVIHDA | 1629.86 | Yes | IL-6R, p 250-263 |

EXAMPLE 1

Synthesis of Peptides—Automated Synthesis

The peptides
RYRAERSKTFT
GQLRAQEEFGQGE
HPSRWAGMGRR and
MVKDLQHHSVIHDA
were synthesized using automated solid phase peptide synthesis. All t-butyloxycarbonyl amino acids were of the L-configuration except for t-butyloxycarbonyl-Gly. The t-butyloxycarbonyl amino acids used included Lys(chlorobenzyloxycarbonyl), Asp($\beta$-benzyl), Glu(-gamma-benzyl), Arg(tosyl), His(benzyloxymethyl), Tyr(2,6-dichlorobenzyl), Ser(0-benzyl) and Thr(0-benzyl). Stepwise buildup of the peptides on Boc-amino acid Pam-resin was conducted on an Applied Biosystem Model 430A peptide synthesizer using the symmetric anhydride program for all amino acids except Gln, Asn, Arg and His; these amino acids were coupled by HOBt esters.

The peptides were cleaved from the peptide resin by treatment with distilled anhydrous HF (10 ml/g peptide resin) in the presence of anisole (1 ml/g peptide resin) and dimethyl sulfide (0.5 ml/g peptide resin for peptides containing Cys and Met) as scavengers. The reaction was carried out at $-5°$ to $0°$ C. for one hour. After removal of the HF under reduced pressure, the resin was washed thrice with diethyl ester. The peptides were extracted from the resin with dilute aqueous acetic acid, concentrated in vacuo, suspended in water or very dilute acetic acid and then lyophilized.

The crude peptides were purified using preparative RP-HPLC (Waters Delta Prep. 3000). The gradient (triethylamine phosphate (TEAP), pH 2.25-2.-6/acetonitrile 0/100 to 30/70) was applied over 30 minutes at 90 ml/min. The fractions were analyzed by Beckman RP-C18 columns and the appropriate fractions were pooled. Desalting of the pooled fractions were carried out on a RP-HPLC column using a 0.5% aqueous acetic acid acetonitrile gradient from 0/100 to 30/70 in 30 min. Highly purified fractions were pooled and lyophilized.

EXAMPLE 2

Synthesis of Peptides—Manual Synthesis

The peptide
GALAENNLNLP
was synthesized using the manual solid phase peptide synthesis procedure. t-Boc-L-Proline was covalently linked to Merrifield resin, $R^1$, via an ester bond to yield Boc-Pro-OR$^1$. The t-butyloxycarbonyl protecting group (t-Boc group) was then selectively removed by treatment of t-Boc-Pro-OR$^1$ with 50% trifluoroacetic acid in methylene chloride at room temperature for 25 minutes. The resin triflouroacetate (TFA Pro-OR$^1$) was then treated with triethylamine solution to neutralize the TFA, and to the resulting amino acyl resin (Pro-OR$^1$) t-Boc-L-leucine and coupling reagent (DCCI) were added. After the coupling reaction was over, the peptide resin was treated with acetic anhydride to block any unreacted amino groups ("capping") that remained after incomplete peptide bond formation. From the protected dipeptide resin (t-Boc-Leu-Pro-OR[1]), by repetition of the above sequence of four steps (deprotection, neutralization, coupling with the next t-Boc-amino acid, and "capping"), the desired peptide, linked to the resin, was obtained. At the end of the synthesis, the N-terminal t-Boc-group was removed from the peptide resin (Steps 1–6).

Each cycle of the synthesis consisted of the following steps:

| Step | Operation | Time (Minutes) |
|---|---|---|
| 1 | $CH_2Cl_2$ wash (3 times) | 3 |
| 2 | Prewash with 50% $TFA/CH_2Cl_2$ | 1 |
| 3 | Deprotection with 50% $TFA/CH_2Cl_2$ | 25 |
| 4 | $CH_2Cl_2$ wash (3 times) | 3 |
| 5 | MeOH wash (3 times) | 3 |
| 6 | $CH_2Cl_2$ wash (3 times) | 3 |
| 7 | Prewash with 10% TEA in $CH_2Cl_2$ | 1 |
| 8 | Neutralization with 10% TEA in $CH_2Cl_2$ | 5 |
| 9 | $CH_2Cl_2$ wash (3 times) | 3 |
| 10 | Treatment with Boc amino acid + Coupling agent in $CH_2Cl_2$ | 90–120 |
| 11 | $CH_2Cl_2$ wash (3 times) | 3 |
| 12 | MeOH wash (3 times) | 3 |
| 13 | $CH_2Cl_2$ wash (3 times) | 3 |
| 14 | Prewash with $Ac_2O/(C_2H_5)_3N/CH_2Cl_2$ | 25 |
| 15 | Acetylation with $Ac_2O/(C_2H_5)_3N/CH_2Cl_2$ | 25 |
| 16 | $CH_2Cl_2$ wash (3 times) | 3 |
| 17 | MeOH wash (2 times) | 2 |

The coupling conditions were as follows:

1. 2 equivalents of t-Boc-amino acid and 2 equivalents of coupling agent were used for each equivalent of peptide resin (t-Boc-Pro-OR[1]).

2. DCCI (Dicyclohexylcarbodiimide) was used as coupling agent. Equivalent amounts of HOBt were added while coupling t-Boc-Asn at positions 7 and 9.

3. t-Boc-Asn at position 6 was coupled via preformed HOBt ester using N-methylpyrrolidone as solvent.

4. The gamma-carboxyl group of glutamic acid residue as protected as a benzyl ester and the amide group of the asparagine residue was unprotected.

HF cleavage was used to cleave the peptide from the resin and remove protecting groups to yield the free peptide. The peptide resin was suspended in anhydrous liquid HF containing anisole as scavenger (10 ml of HF and 1 ml of anisole for each gram of resin) and stirred at $-5°$ to $0°$ C. for one hour. After removal of HF under vacuum, the resin was washed with ether and treated with IN acetic acid to extract the peptide. Lyophilization of the acetic acid extract yielded the peptide as HF salt.

Purification was achieved by treatment of the crude peptide with acetic acid and TEAP buffer (pH 2.25–2.6) to extract out the side products, yielding the pure peptide as a gelatinous solid. This solid was dissolved in a mixture of acetic acid, water and acetonitrile; the solution was then stirred with AG3-X4a resin (acetate form) to exchange the $F^-$ from the peptide. The filtrate on lyophilization yielded the pure peptide as acetate salt.

Purity analysis by HPLC was 98.53%. Amino acid analysis agreed with the peptide structure. A test for fluoride was negative.

EXAMPLE 3

Inhibition of; IL-6 Mediated Proliferation of B9.9 cells

IL-6 antagonist activity of the subject peptides was measured using the IL-6 dependent B9.9 hybridoma cell line as described in Brakenhoff et al., J. Immunol. 139:4116, 1987. Recombinant IL-6 was purchased from Genzyme, Inc. and Amgen. The B9.9 hybridoma cell line was obtained from Scripps Clinic. B9.9 cells were grown in culture supplemented with IL-6-containing supernatant from stimulated fibroblasts, and split every 2–3 days. Only cultures with greater than 95% viable cells were used for bioassays. The fibroblast cell line GM02571 was obtained from the Human Genetic Mutant Cell Repository Institute for Medical Research. IL-6 containing supernatant (F-IL-6) was produced by stimulating confluent GM02571 fibroblasts with 50 $\mu$g/ml polyriboinosinic-polyribocytidylic acid obtained from CalBiochem.

$1 \times 10^4$ cells were cultured in presence of 4-fold serial dilutions (1:16 to 1:65,536) of F-IL-6 in RPMI supplemented with 10% fetal calf serum, 2 mM L-glutamine, and $5 \times 10^{-5}$ M 2-mercaptoethanol in flat bottom microtiter plates. After 2 days the cells were incubated for 4 hours with 3-(4,5-dimethylthiazol-2-yl)-diphenyl tetrazolium bromide (MTT) and the absorbance was measured at 570–650 nm as described in Mosmann, J. Immunol. Meth. 65:55, 1983. Background values from cells which did not receive IL-6 were subtracted from all data points. One unit of IL-6 was defined as the amount of IL-6 required to obtain half maximal proliferation and was calculated by probit analysis.

Antagonist activity was measured in two different ways; first, a fixed amount of IL-6 (1–10 U/ml) was incubated with increasing amounts of peptides. Second, serial dilutions of an IL-6 containing supernatant or recombinant IL-6 were incubated with fixed amounts of peptide. This second approach allows for probit analysis and is therefore the preferred method. The peptides were preincubated with IL-6 for variable times (0–5 h) in both approaches in serum-free RPMI before the cells were added.

Figure 1:
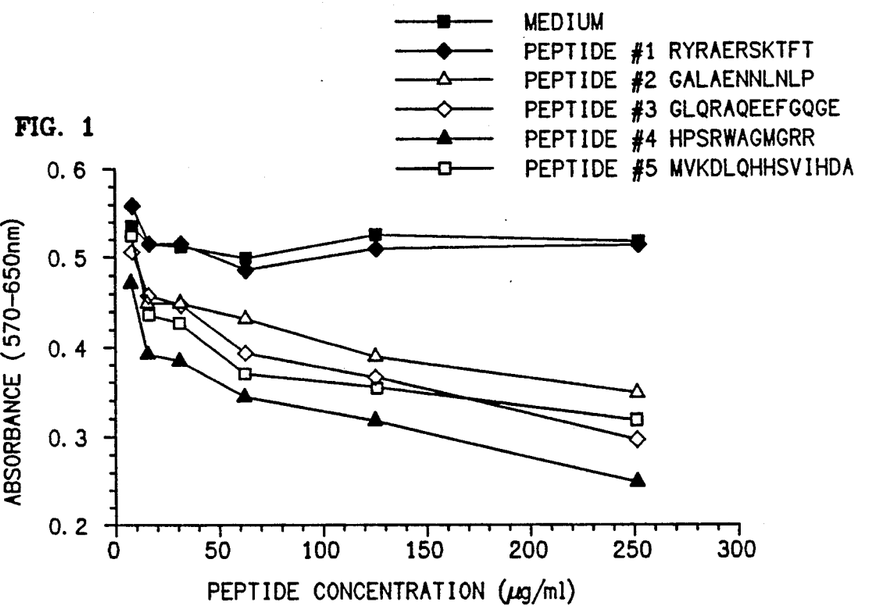
FIG. 1 shows the dose response curve for inhibition of IL-6 mediated proliferation of B9.9 cells obtained by addition of a fixed amount of IL-6 and various amounts of peptides.

As shown in FIG. 1, the growth of B9.9 cells was significantly inhibited in a dose-dependent manner in presence of three IL-6R-derived peptides (GQLRAQEEFGQGE, HPSRWAGMGRR, and MVKDLQHHSVIHDA) and one IL-6 derived peptide (GALAENNLNLP). A fourth IL-6R-derived peptide (RYRAERSKTFT) was found to be inactive.

Figure 2A:
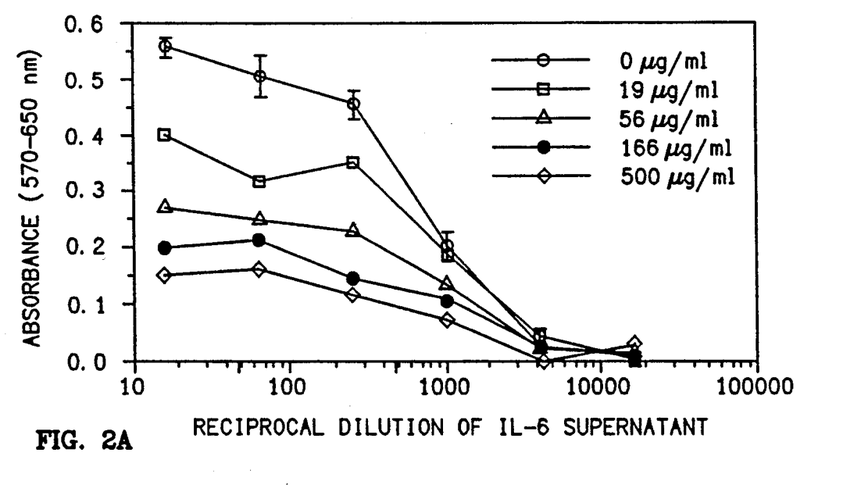
FIGS. 2A and 2B show inhibition of IL-6 mediated proliferation of B9.9 cells in the presence of peptides. The activity in a standard preparation of IL-6 containing fibroblast supernatant is determined in the presence of various amounts of peptides.
Figure 2B:
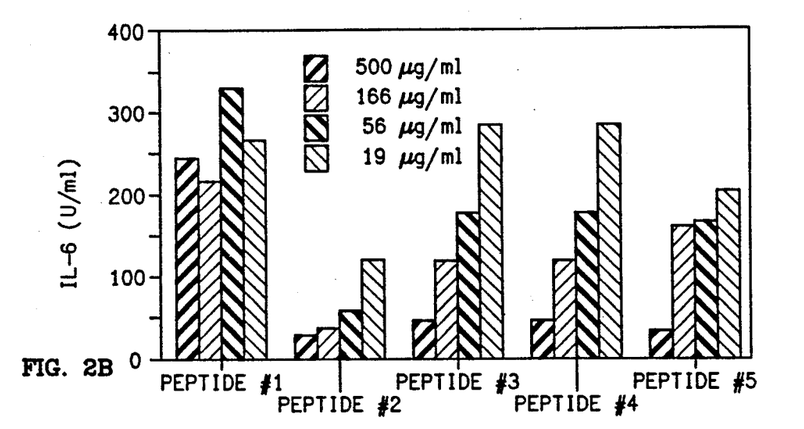

This effect was better detected in a second set of experiments when various concentrations of peptides were incubated in presence of several serial dilutions of fibroblast-derived IL6 (FIGS. 2A and 2B). This protocol allows for the calculation of IL-6 units as a measurement for IL-6 activity.

Figure 3:
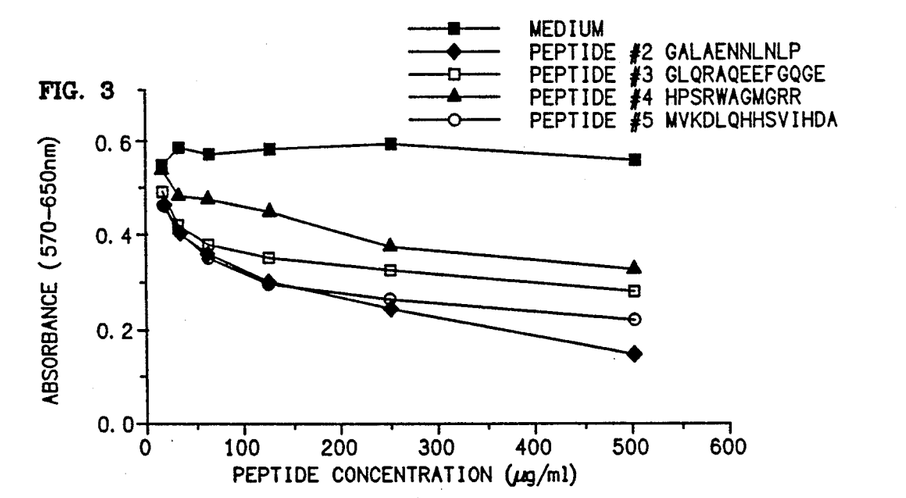
FIG. 3 shows that the peptides are able to inhibit the proliferation of B9.9 cells induced by murine IL-6.

Significant inhibition was obtained with concentrations in the micromolar range. Similar results were obtained when either human recombinant IL-6 or IL-6-containing supernatants from LPS-stimulated Balb/c peritoneal macrophage cultures were used in the assay (FIG. 3).

Additional peptides of the invention have been synthesized and tested in the B9.9 cell proliferation assay as described above, and have similarly been shown to be active as IL-6 antagonists. Table 2 sets forth proliferation inhibition data for such compounds.

TABLE 2

Inhibition of IL-6 mediated proliferation of
B9.9 cells (peptide concentration = 250 μM)

| Peptide Sequence | Percent Inhibition |
| --- | --- |
| GALAENNLNLP | 97 ± 2 |
| ESSKEALAEN | 78 ± 9 |
| NLNLPKMAEK | 43 ± 38 |
| ALAENNLNLP | 30 ± 36 |
| LAENNLNLP | 30 ± 34 |
| GALAENNLNL | 82 ± 16 |
| GALAENNLNLP-NH2 | 80 ± 15 |
| Ac-GALAENNLNLP | 61 ± 36 |
| GGLAENNLNLP | 79 ± 9 |
| GAAAENNNLNLP | 29 ± 19 |
| GALGENNLNLP | 15 ± 29 |
| GALAANNLNLP | 45 ± 35 |
| GALAEANLNLP | 36 ± 35 |
| GALAENALNLP | 33 ± 51 |
| GALAENNANLP | 77 ± 21 |
| GALAENNLALP | 60 ± 5 |
| GALAENNLNAP | 56 ± 27 |
| GQLRAQEEFGQGE | 97 ± 3 |
| GQLRAQEEFGQG | 71 ± 19 |
| GQLRAQEEFG | 86 ± 9 |
| GQLRAQEEF | 97 ± 3 |
| GQLRAQEE | 81 ± 9 |
| GQLRAQ | 70 ± 25 |
| Ac-GQLRAQEEFGQGE-NH2 | 92 ± 6 |
| RHVVQLRAQEE | 99 ± 1 |
| EFGQGEWSEWS | 77 ± 7 |
| HPSRWAGMGRR | 91 ± 2 |
| GMGRRLLLRS | 49 ± 44 |
| AGSHPSRWAG | 59 ± 46 |
| MVKDLQHHSVIHDA | 98 ± 1 |
| HSVIHDAWSGL | 28 ± 39 |
| AGDFQEPSQYSQE | 84 ± 11 |
| RLFQNSPAGDFQ | 43 ± 64 |
| EPSQYSQESQLF | 95 ± 2 |
| AGDFQEPSQYSQ | 47 ± 17 |
| AGDFQE | 67 ± 7 |
| AGDFQEPSQY | 81 ± 3 |
| AGDFQEPSQYSQE-NH2 | 71 ± 9 |
| Ac-AGDFQEPSQYSQE | 46 ± 50 |

The above results indicate that the described peptides have IL-6 antagonist activity. This is a unique, and perhaps the first, description of IL-6 antagonist peptides. The IL-6 antagonist activity was measured as the inhibition of IL-6 induced proliferation of a mouse hybridoma cell line (B9.9 assay). Other commonly used bioassays are available to measure the enhancement of immunoglobulin production in a B cell line, e.g., CESS (CESS assay) or SKW6.4 (SKW6.4 assay) in response to IL-6. IL-6 activity measured in the B9.9 assay usually correlate with the IL-6 activity determined in the CESS or SKW6.4 assay. It is anticipated that the present antagonistic peptides would similarly be active in the CESS assay, and can be employed therein.

EXAMPLE 4

PHA-induced proliferation of human peripheral blood lymphocytes

Stimulation of T cells with PHA induces, among many other effects, the production of interleukin 2 and the induction of its receptor. The interaction of IL-2 with its receptor is crucial for the expansion of the T cell population. An ideal IL-6 antagonist peptide should have no cytotoxic side effects and be specific for IL-6 and, therefore, show no effect on an IL-2-mediated response. Therefore, peptides were added to human peripheral blood cells stimulated by optimal amounts of PHA.

Figure 4:
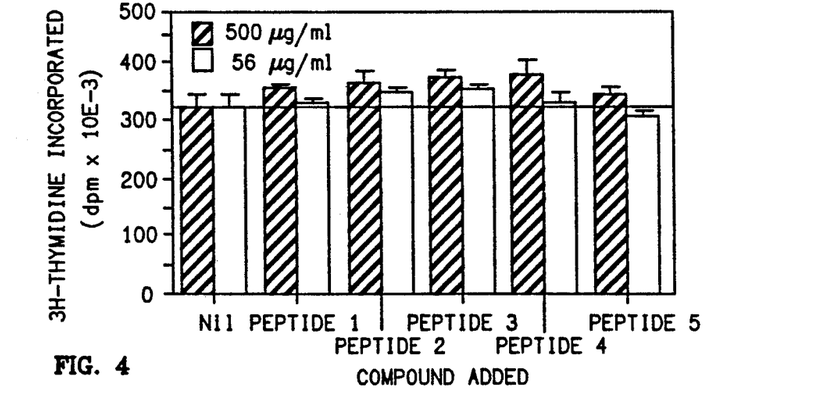
FIG. 4 shows that representative peptides of the invention are not cytotoxic and do not inhibit mitogen-induced proliferation of human peripheral blood lymphocytes.

Lymphocytes from human peripheral blood were isolated by Ficoll density gradient centrifugation of heparinized blood from healthy volunteers. The cells ($1 \times 10^6$/ml) were cultured (37° C., 5% $CO_2$) in 0.2 ml RPMI 1640 supplemented with 2 mM L-glutamine, 10% fetal calf serum, and 1% penicillin/streptomycin in microtiter plates in presence of 2 μg/ml phytohemagglutinin (PHA) plus 500 μg/ml or 56 μg/ml of the indicated peptides. DNA synthesis was measured on day 3 by a terminal 5 hour pulse of cultures with [$^3$H]-thymidine. None of the peptides was able to inhibit the PHA-induced proliferation significantly and reproducibly when tested at 100 μg/ml or 500 μg/ml (FIG. 4).

This result suggests that none of the tested peptides is cytotoxic and that the peptides are unlikely to interfere with IL-2-mediated proliferation.

EXAMPLE 5

Coupling of Modified Peptides With Protein Carrier Molecules

Modified peptides were synthesized with a glycine residue as a spacer and an N-terminal free cysteine moiety suitable for coupling to carrier molecules. The following modified peptides were prepared:

```
C G H P S R W A G M G R R
C G Q L R A Q E E F G Q G E
C G A G D F Q E P S Q Y S Q E
C G A L A E N N L N L P
C G M V K D L Q H H S V I H D A
C G R Y R A R S K T F T
```

The above cysteine-containing peptides were coupled to keyhole limpet hemocyanin (KLH) using MBS via the cysteinyl sulfhydryl group as described in Green et al., Cell 28:477, 1982.

The synthetic peptides may also be conjugated to bovine serum albumin (BSA), porcine thyroglobulin (PTG), or other antigenic proteins using the heterobifunctional crosslinking agent m-maleimidobenzoyl-N-hydroxysuccinimide ester (MBS) (Pierce Chemical Co.). The protein is suspended in ml of 50 mM $NaPO_2$ (pH 7.0) to which MBS dissolved in DMF (10 mg/ml) is slowly added. The reaction is allowed to proceed for minutes at room temperature with slow stirring. Carrier proteins derivatized with MBS are combined with synthetic peptide in 50 mM $NaPO_4$ (pH 7.0) for 3–5 hours at room temperature. The conjugates are dialyzed at 4° C. overnight and analyzed by SDS-PAGE.

EXAMPLE 6

Generation of Antibodies to Peptide/Protein Conjugates

Polyclonal anti-peptide antibodies were generated in rabbits against the modified peptides listed in Example 5 as conjugated to KLH.

Rabbits were immunized subcutaneously with 200 μg conjugated peptide emulsified in Complete Freund's Adjuvant. Booster injections with 200 μg conjugated peptide were given every three weeks in RIBI Adjuvant system. Immune serum was collected weekly starting 1 week after the third injection.

Therapeutic Utility of the Subject Compounds

Elevated serum levels of IL-6 have been observed in several diseases such as rheumatoid arthritis (Al-Balaghi et al., Immunol. Rev. 78:7, 1984), and systemic lupus erythematosus (Tanaka, et al., J. Immunol. 141:3043, 1988), and it has been suggested that IL-6 is an important contributing factor to the autoantibody production observed in these patients (Nawata et al., Ann. New York Academy of Sciences 557:230, 1989). Multiple sclerosis is also characterized by high levels of autoantibodies but IL-6 levels have not yet been reported in this context. In addition, elevation of serum IL-6 and acute phase responses have been reported in patients with severe burns (Nijsten, et al., Lancet ii:921, 1987), with acute bacterial infections (Helfgott, et al., J. Immunol. 142:948, 1989), with meningococcal septic shock (Waage, et al., J. Exp. Med. 169:333, 1989), following injection with tumor necrosis factor α or interleukin 2 (Jablons, et al., J. Immunol. 142:1542, 1989), and following surgical operations (Nishimoto, et al., Clin. Immunol. Immunopathol. 50:399, 1989). Based on in vitro experiments it has been suggested that IL-6 is also involved in viral diseases (Sehgal, et al., J. Exp. Med. 167:1951, 1988), including HIV-infection (Nakajima, et al., J. Immunol. 142:531, 1989). Furthermore, human myeloma cells express high amounts of IL-6 receptor molecules and IL-6 has been advanced as a principal autocrine factor (Hirano, et al., Nature 332,83, 1988). Additional therapeutic uses of the present peptides may be found with regard to IL-6 and IL-6 receptor related pathologies as described by Kishimoto (Blood 74:1, 1989). IL-6 antagonist peptides may, therefore, be therapeutically useful in treatment of such diseases, and in other IL-6 associated diseases characterized by elevated IL-6 or IL-6 receptor levels, by reducing autoantibody production, by limiting the production of acute phase proteins, or through other modulation of IL-6 or IL-6 receptor-mediated pathology. Furthermore, these peptides may be useful in reducing side effects of cytokine treatment protocols in cancer patients and in treatment of myeloma patients.

Because IL-6 is a pluripotent cytokine which is likely to participate in a wide variety of immune responses, it is expected that peptides which regulate IL-6 function will have broad therapeutic utility in many mammalian diseases. It is expected that these peptides will inhibit or enhance immune responses by modulating IL-6 function in humans or other mammals. As such, therapeutic use of these peptides is expected to be beneficial in treating a variety of IL-6 associated diseases, many of which are currently treated with immunomodulators or immunosuppressants. Such IL-6 associated diseases include

- Autoimmune disorders generally (including organ specific and systemic diseases, e.g., SLE, rheumatoid arthritis, diabetes and multiple sclerosis)
- Infectious diseases (bacterial and viral infection; septic shock)
- Inflammatory diseases in general, including immunoinflammatory diseases
- Immune deficiency diseases, including AIDS
- Hematologic diseases (e.g., plasma cell dyscrasias, leukemia, lymphoma)
- Allergic diseases (Type I-IV)
- Organ transplantation reactions
- Multiple myelomas/plasmacytomas
- Castleman's disease
- Lennart's T-cell lymphoma
- Non-Hodgkin's lymphoma
- Cardiac myxoma
- Mesangial proliferative glomerulonephritis
- Polyclonal B-cell activation conditions
- Abnormal acute phase protein (e.g., CRP, serum amyloid A protein and/or "heat shock protein") production conditions It is to be understood that the examples described herein are for illustrative purpose only and that various modifications or changes in light thereof will be recognized by persons skilled in the art and are to be included within the purview of this application and the scope of the appended claims.

We claim:

1. A peptide of the formula $$X^2-(X^1-)7-8-9-10-11-12-14(-Y^1)-Y^2 \quad (II)$$

and pharmaceutically acceptable salts thereof, wherein 7 is selected from L; I and A; and V, Nle, Sar, β-Ala and Aib;

8 is selected from A; L and I; and V, Nle, Sar, β-Ala and G;

9 is selected from E; pyro-Glu; and D, S, T, Y, β-Asp and 3-Glu;

10 is selected from N; Q, M, W and F; and Y;

11 is selected from N; Q, M, W and F; and Y;

12 is selected from L; I and A; and V, Nle, Sar, β-Ala and Aib;

13 is selected from N; Q, M, W and F; and Y; and 14 is selected from L; I and A; and V, Nle, Sar, β-Ala and Aib;

$X^1$ is optional and, where present, is selected from

```
              6—
           5—6—
        4—5—6—
     3—4—5—6—
  2—3—4—5—6— and
1—2—3—4—5—6—
``` wherein 1 is selected from E; pyro-Glu; and D, S, T, Y, β-Asp and 3-Glu;

2 is selected from S; A and M; and T, HomoSer and Y;

3 is selected from S; A and M; and T, HomoSer and Y;

4 is selected from K; and R, Orn, HomoArg and H;

5 is selected from E; G and pyro-Glu; and D, S, T, Y, β-Asp and 3-Glu;

6 is selected from A; L and I; and V, Nle, Sar, β-Ala and G;

wherein one or more D-amino acids may be employed among residues 1 to 6;

$Y^1$ is optional and, where present, is selected from

```
—15
—15—16
—15—16—17
—15—16—17—18
—15—16—17—18—19 and
—15—16—17—18—19—20
``` wherein 15 is selected from P; L and I; and V, Aib, hydroxy-Pro and HomoPro;

16 is selected from K; and R, Orn, HomoArg and H;

17 is selected from M; W, F and Q; and N, Y, H, α-naphthylalanine and β-naphthylalanine;

18 is selected from A; L and I; and V, Nle, Sar, β-Ala and G;

19 is selected from E; pyro-Glu; and D, S, T, Y, β-Asp and 3-Glu;

20 is selected from K; and R, Orn, HomoArg and H; and wherein one or more D-amino acids may be employed among residues 15 to 20;

$X^2$ is a $N^\alpha$-substituent selected from hydrogen, R'CO— and R'—;

$Y^2$ is a carboxyl-terminal substituent selected from hydroxyl, —NH$_2$, —NHR', —NR'$_2$, —OR' and —NHNH$_2$; and wherein each R' is individually a pharmaceutically suitable substituent group.

2. A compound of claim 1 wherein each R' is individually selected from linear and branched, unsubstituted and substituted $C_1$-$C_8$ lower alkyls, $C_2$-$C_8$ alkenyls, $C_2$-$C_8$ alkynyls, $C_6$-$C_{14}$ aryls, $C_7$-$C_{14}$ ; alkaryls, $C_7$-$C_{14}$ aralkyls and $C_3$-$C_{14}$ cycloalkyls, and, in the case of —NR'$_2$, from cyclized groups forming (in attachment with the nitrogen atom) a 5–8 membered saturated heterocyclic ring optionally containing an oxygen or nitrogen as a further ring heteroatom.

3. A compound of claim 1 wherein 1 is E; 2 is S; 3 is S; 4 is K; 5 is E; 6 is A; 7 is L; 8 is A; 9 is E; 10 is N; 11 is N; 12 is L; 13 is N; 14 is L; 15 is P; 16 is K; 17 is M; 18 is A; 19 is E; and 20 is K.

4. A compound of claim 1 wherein at least seven members among positions 7 to 14 have an amino acid sequence selected from the group consisting of:

7(L)8(A)9(E)10(N)11(N)12(L)13(N);
7(L)9(E)10(N)11(N)12(L)13(N)14(L);
7(L)8(A)10(N)11(N)12(L)13(N)14(L);
7(L)8(A)9(E)11(N)12(L)13(N)14(L);
7(L)8(A)9(E)10(N)12(L)13(N)14(L);
7(L)8(A)9(E)10(N)11(N)13(N)14(L);
7(L)8(A)9(E)10(N)11(N)12(L)14(L); and
8(A)9(E)10(N)11(N)12(L)13(N)14(L).

5. A compound of claim 1 having an amino acid sequence selected from

G A L A E N N L N L P
G A L A E N N L N L
G A L A E N N L N L P—NH$_2$.

6. A peptide of the formula $X^c-(X^1-)7-8-9-10-11-12-13-14(-Y^1-)-Y^c$ and pharmaceutically acceptable salts thereof, wherein
7 is selected from L; I and A; and V, Nle, Sar, β-Ala and Aib;
8 is selected from A; L and I; and V, Nle, Sar, β-Ala and G;
9 is selected from E; pyro-Glu; and D, S, T, Y, β-Asp and 3-Glu;
10 is selected from N; Q, M, W and F; and Y;
11 is selected from N; Q, M, W and F; and Y;
12 is selected from L; I and A; and V, Nle, Sar, β-Ala and Aib;
13 is selected from N; Q, M, W and F; and Y; and
14 is selected from L; I and A; and V, Nle, Sar, β-Ala and Aib;
$X^1$ is optional and, where present, is selected from

6—

5—6—

4—5—6—

3—4—5—6—

2—3—4—5—6— and

1—2—3—4—5—6— wherein
1 is selected from E; pyro-Glu; and D, S, T, Y, β-Asp and 3-Glu;
2 is selected from S; A and M; and T, HomoSer and Y;
3 is selected from S; A and M; and T, HomoSer and Y;
4 is selected from K; and R, Orn, HomoArg and H;
5 is selected from E; G and pyro-Glu; and D, S, T, Y, β-Asp and 3-Glu;
6 is selected from A; L and I; and V, Nle, Sar, β-Ala and G;

wherein one or more D-amino acids may be employed among residues 1 to 6;
$Y^1$ is optional and, where present, is selected from

—15

—15—16

—15—16—17

—15—16—17—18

—15—16—17—18—19 and

—15—16—17—18—19—20 wherein
15 is selected from P; L and I; and V, Aib, hydroxy-Pro and HomoPro
16 is selected from K; and R, Orn, HomoArg and H;
17 is selected from M; W, F and Q; and N, Y, H, α-naphthylalanine and β-naphthylalanine;
18 is selected from A; L and I; and V, Nle, Sar, β-Ala and G;
19 is selected from E; pyro-Glu; and D, S, T, Y, β-Asp and 3-Glu;
20 is selected from K; and R, Orn, HomoArg and H; and wherein one or more D-amino acids may be employed among residues 15 to 20; and wherein one of $X^c$ and $Y^c$ is present and is a moiety suitable for coupling the peptide to another molecule.

7. A peptide of the formula $X^2-(X^1-)3-4-5-6-7(-Y^1-)-Y^2$ (III)

and pharmaceutically acceptable salts thereof, wherein
3 is selected from S; A and M; and T, HomoSer and Y;
4 is selected from K; and R, Orn, HomoArg and H;
5 is selected from E; G and pyro-Glu; and D, S, T, Y, β-Asp and 3-Glu;
6 is selected from A; L and I; and V, Nle, Sar, β-Ala and G;
7 is selected from L; I and A; and V, Nle, Sar, β-Ala and Aib;
wherein one or more D-amino acids may be employed among residues 3 to 7;
$X^1$ is optional and, where present, is selected from 2— and -continued

1—2— wherein
1 is selected from E; pyro-Glu; and D, S, T, Y, β-Asp and 3-Glu; and
2 is selected from S; A and M; and T, HomoSer and Y;

$Y^1$ is optional and, where present, is selected from

—8

—8—9 and

—8—9—10 wherein
8 is selected from A; L and I; and V, Nle, Sar, β-Ala and G;
9 is selected from E; pyro-Glu; and D, S, T, Y, β-Asp and 3-Glu;
10 is selected from N; Q, M, W and F; and Y;
and wherein
$X^2$ is a $N^\alpha$-substituent selected from hydrogen, R'CO— and R'—;
$Y^2$ is a carboxyl-terminal substituent selected from hydroxyl, —NH$_2$, —NHR', —NR'$_2$, —OR' and —NHNH$_2$; and
wherein each R' is individually a pharmaceutically suitable substituent group.

8. A compound of claim 7 wherein at least four members among positions 3 to 7 have an amino acid sequence selected from the group consisting of: 3(S)4(K)5(E)6(A); 3(S)5(E)6(A)7(L); 3(S)4(K)6(A)7(L); 3(S)4(K)5(E)7(L); and 4(K)5(E)6-(A)7(L).

9. A compound of claim 7 having the amino acid sequence

E S S K E A L A E N.

10. A peptide of the formula $$X^2—11—12—13—14—15—16(—Y^1)—Y^2 \quad (IV)$$

and pharmaceutically acceptable salts thereof, wherein
11 is selected from N; Q, M, W and F; and Y;
12 is selected from L; I and A; and V, Nle, Sar, β-Ala and Aib;
13 is selected from N; Q, M, W and F; and Y;
14 is selected from L; I and A; and V, Nle, Sar, β-Ala and Aib;
15 is selected from P; L and I; and V, Aib, hydroxy-Pro and HomePro;
16 is selected from K; and R, Orn, HomoArg and H; wherein one or more D-amino acids may be employed among residues 15 to 16;

$Y^1$ is optional and, where present, is selected from

—17

—17—18

—17—18—19 and

—17—18—19—20 wherein
17 is selected from M; W, F and Q; and N, Y, H, α-naphthylalanine and β-naphthylalanine;
18 is selected from A; L and I; and V, Nle, Sar, β-Ala and G;
19 is selected from E; pyro-Glu; and D, S, T, Y, β-Asp and 3-Glu;
20 is selected from K; and R, Orn, HomoArg and H; and wherein one or more D-amino acids may be employed among residues 17 to 20;
and wherein
$X^2$ is a $N^\alpha$-substituent selected from hydrogen, R'CO— and R'—;
$Y^2$ is a carboxyl-terminal substituent selected from hydroxyl, —NH$_2$, —NHR', —NR'$_2$, —OR' and —NHNH$_2$; and
wherein each R' is individually a pharmaceutically suitable substituent group.

11. A compound of claim 10 wherein at least five members among positions 11 to 16 have an amino acid sequence selected from the group consisting of: 11(N)12(L)13(N)14(L)15(P); 12(L)13(N)14(L)15(P)16(K); 11(N)13(N)14(L)15(P)16(K); 11(N)12(L)14(L)15(P)16(K); and 11(N)12(L)13(N)14(L)16(K).

12. A compound of claim 10 having the amino acid sequence
N L N L P K M A E K.

13. A pharmaceutical composition comprising a compound of claim 1 pharmaceutically acceptable carrier.

14. A pharmaceutical composition comprising a compound of claim 7 pharmaceutically acceptable carrier.

15. A pharmaceutical composition comprising a compound of claim 10 pharmaceutically acceptable carrier.

* * * * *